(12) United States Patent
Pohlmeier

(10) Patent No.: US 8,900,172 B2
(45) Date of Patent: Dec. 2, 2014

(54) METHOD FOR CONTROLLING A BLOOD TREATMENT APPARATUS, CONTROL DEVICE, DISPENSING DEVICE AND BLOOD TREATMENT APPARATUS

(75) Inventor: Robert Pohlmeier, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/365,383

(22) Filed: Feb. 3, 2012

(65) Prior Publication Data
US 2012/0203159 A1 Aug. 9, 2012

Related U.S. Application Data

(60) Provisional application No. 61/439,387, filed on Feb. 4, 2011.

(30) Foreign Application Priority Data

Feb. 4, 2011 (DE) .......................... 10 2011 010 406

(51) Int. Cl.
*A61M 37/00* (2006.01)
*A61M 1/36* (2006.01)
*A61M 1/34* (2006.01)

(52) U.S. Cl.
CPC ........... *A61M 1/3675* (2013.01); *A61M 1/3437* (2014.02)
USPC ...................................... 604/4.01

(58) Field of Classification Search
CPC ... A61M 1/16; A61M 1/1601; A61M 1/1603; A61M 1/3403; A61M 1/341; A61M 1/3441; A61M 1/3444; A61M 1/3448; A61M 1/3451

USPC ................................................. 604/4.01–6.16
See application file for complete search history.

(56) References Cited

U.S. PATENT DOCUMENTS 5,609,770 A * 3/1997 Zimmerman et al. ........ 210/739
(Continued)

FOREIGN PATENT DOCUMENTS

| AT | 505690 A1 | 3/2009 |
|---|---|---|
| DE | 101 14 283 A1 | 7/2002 |

(Continued)

*Primary Examiner* — Philip R Wiest
*Assistant Examiner* — Benjamin Klein
(74) *Attorney, Agent, or Firm* — Kenyon & Kenyon LLP

(57) ABSTRACT

The present invention relates to a method for controlling or regulating an apparatus for extracorporeally treating blood in an extracorporeal blood circuit while adding citrate and calcium for the purpose of anticoagulation. The apparatus comprises a dispensing device for dispensing a calcium solution into the extracorporeal blood circuit. The method encompasses outputting a signal to the dispensing device for altering a setting of the dispensing device, in which the setting corresponds to or effects an addition of calcium, a calcium dosage, concentration, amount or rate. The method further encompasses defining or altering the signal with regard to a calcium content or a calcium concentration of a substituate solution used in extracorporeally treating the blood, and detecting the range of values of permissible or allowed settings for the calcium introduced or to be introduced into the extracorporeal blood circuit by the dispensing device, particularly its amount, concentration or dosage.

10 Claims, 3 Drawing Sheets

(56) References Cited

U.S. PATENT DOCUMENTS

| | | |
|---|---|---|
| 2005/0085760 A1 | 4/2005 | Ware et al. |
| 2007/0066928 A1 | 3/2007 | Lannoy |
| 2009/0221948 A1 | 9/2009 | Szamosfalvi et al. |
| 2011/0208105 A1* | 8/2011 | Brandl et al. ................ 604/5.01 |
| 2011/0288464 A1* | 11/2011 | Lannoy ........................ 604/6.07 |
| 2012/0265116 A1* | 10/2012 | Szamosfalvi et al. ....... 604/6.07 |
| 2013/0274644 A1* | 10/2013 | Hertz ........................... 604/6.09 |

FOREIGN PATENT DOCUMENTS

| | | | |
|---|---|---|---|
| DE | 103 17 024 A1 | 11/2004 | |
| WO | 2004/089440 A1 | 10/2004 | |
| WO | 2009/026603 A2 | 3/2009 | |
| WO | WO 2009026603 A1 * | 3/2009 | ............ A61M 1/34 |
| WO | 2010/029401 A2 | 3/2010 | |

\* cited by examiner

METHOD FOR CONTROLLING A BLOOD TREATMENT APPARATUS, CONTROL DEVICE, DISPENSING DEVICE AND BLOOD TREATMENT APPARATUS

CROSS-REFERENCE TO RELATED APPLICATIONS

The present application claims priority to U.S. Provisional Application Ser. No. 61/439,387, filed on Feb. 4, 2011, and claims priority to Application No. DE 10 2011 010 406.2, filed in the Federal Republic of Germany on Feb. 4, 2011, each of which is expressly incorporated herein in its entirety by reference thereto.

FIELD OF INVENTION

The present invention relates to a method for controlling or regulating an apparatus for extracorporeally treating blood. It further relates to a control device, a user interface, a device for dispensing or adding a calcium solution into the extracorporeal blood circuit and an apparatus for extracorporeally treating blood. Furthermore, the present invention relates to a digital storage medium, a computer program product as well as a computer program.

BACKGROUND INFORMATION

In certain extracorporeal blood treatments, a coagulation prophylaxis takes place in order to prevent coagulation of the extracorporeally conducted blood. In a known method that serves this purpose, a coagulation tendency of the blood flowing extracorporeally is reduced by initially adding citrate to the blood. By adding the citrate, calcium is increasingly permeably transferred through the membrane of the utilized filter. This and also using solutions during the blood treatment that do not comprise calcium, lead to a calcium loss from the blood. After having treated the blood, calcium in the form of a calcium-containing solution is added to the blood before it is returned into the body of the patient. Methods and apparatuses for determining an amount or concentration of calcium necessary for achieving this effect are known from practice.

SUMMARY

One object of the present invention is to propose a further method for controlling or regulating an apparatus for extracorporeally treating blood while adding citrate ("Ci") and calcium ("Ca"). Further, a suited control device, a corresponding user interface as well as devices and apparatuses are to be specified.

An object according to the present invention is accomplished by a method having the features described herein. It is further accomplished by a control device having the features described herein, a user interface having the features described herein, a device having the features described herein and an apparatus having the features described herein. An object according to the present invention is further accomplished by a digital storage medium, a computer program product and a computer program having the features described herein.

According to the present invention, a method for controlling or regulating an apparatus serving to extracorporeally treat blood, wherein the blood is treated in an extracorporeal blood circuit while adding citrate for anticoagulation or coagulation prophylaxis, is proposed. The regulated or controlled apparatus moreover comprises a dispensing device for dispensing a calcium solution into the extracorporeal blood circuit. Alternatively, the method according to the present invention serves to control or regulate such dispensing device.

The method according to the present invention encompasses establishing or detecting and/or outputting a signal to the dispensing device for altering a setting of the dispensing device, by which calcium is added to the blood flowing extracorporeally. Hereby, the setting corresponds to a delivery of calcium, a calcium dose, concentration, amount or rate, or effects such.

The method according to the present invention further encompasses defining or altering the signal with regard to calcium content or calcium concentration of a substitute solution used in or for extracorporeally treating the blood.

Furthermore, the method according to the present invention encompasses detecting the range of permissible or allowed settings (or the range for setting) for the calcium introduced or to be introduced into the extracorporeal blood circuit by the dispensing device, particularly its amount, concentration or dosage.

The control device according to the present invention is provided and/or programmed for executing the method according to the present invention.

The user interface according to the present invention comprises a control device according to the present invention and/or is functionally connected with such. The user interface according to the present invention comprises an input device. The input device is provided for indicating or inputting (in the sense of communicating) a calcium dosage, amount or concentration by the operator or user of the user interface, the addition of which is to be initiated or effected by the control device.

The input device may be a key or a keyboard, a slide bar, a touch screen or an otherwise prepared display or device for inputting data, a computer mouse, or the like.

The device according to the present invention for dispensing a calcium solution into the extracorporeal blood circuit is programmed for executing, particularly for automatically executing, the method according to the present invention and/or is accordingly controlled by the control device according to the present invention.

The apparatus according to the present invention is provided for extracorporeally treating blood. It is further designed or provided for performing or executing the method according to the present invention and/or comprises at least one control device according to the present invention, and/or a device according to the present invention for dispensing a calcium solution into the extracorporeal blood circuit and/or a user interface according to the present invention.

All advantages resulting from the method according to the present invention may undiminishedly also be achieved by any of the subjects according to the present invention. In some embodiments according to the present invention, this also applies for the digital storage medium according to the present invention, the computer program product according to the present invention and the computer program according to the present invention.

A digital storage medium according to the present invention, particularly in the form of a disk, CD, DVD or EPROM, particularly with electronically or optically readable control signals, may interact with a programmable computer system such that the mechanical steps of a method according to the present invention are prompted.

Hereby, all, several or some of the mechanically executed steps of the method according to the present invention may be prompted.

A computer program product according to the present invention comprises a program code stored on a machine-readable carrier for prompting the mechanical steps of the method according to the present invention when the computer program product runs on a computer.

A machine-readable data storage device denotes in certain embodiments of the present invention a medium that contains data or information which is interpretable by software and/or hardware. The medium may be a disk, a CD, DVD, a USB stick, a flash card, an SD card or the like.

A computer program according to the present invention comprises a program code for prompting the mechanical steps of a method according to the present invention when the computer program runs on a computer.

It also applies for the computer program product according to the present invention and the computer program according to the present invention that all, several or some of the mechanically executed steps of the method according to the present invention are prompted.

Exemplary embodiments according to the present invention may comprise one or more of the features described herein.

In all of the following exemplary embodiments, the use of the expression "may be" or "may have" and so on, is to be understood synonymously with "preferably is" or "preferably has," respectively, and so on, and is intended to illustrate certain embodiments according to the present invention.

In certain embodiments according to the present invention, the dispensing device for dispensing a calcium solution into the extracorporeal blood circuit is a pump, in particular a calcium pump.

In certain embodiments, the dispensing device for dispensing a calcium solution is exclusively provided for dispensing calcium solution for achieving a calcium balance or a calcium compensation.

Detecting the range of permissible or allowed settings—which is in some embodiments according to the present invention performed automatically or by corresponding apparatuses—for the calcium introduced or to be introduced into the extracorporeal blood circuit by the dispensing device, particularly its amount, concentration or dosage, in certain embodiments according to the present invention takes place again with each setting or modification. In some embodiments according to the present invention, detecting takes place several times during a blood treatment, where required. The range of values or the lowest value are thus dynamically detected in some embodiments according to the present invention.

In some embodiments according to the present invention, detecting the range of values or values range of a permissible or allowed range of settings or a range for setting is determining a range of values of a permissible or allowed range of settings or a range for setting, in particular a range of settings or a range for setting which is offered or exclusively offered to the user or setter—for example, in a user interface or by a switch configuration. In these embodiments of the present invention, a setting of values which are beyond or outside the setting range is excluded for the user. An alternative to excluding these values or in addition hereto, outputting a displaying or an alarm may take place if or when such values should be set.

In certain embodiments according to the present invention, detecting the values range of a permissible or allowed range of settings takes place automatically or by a corresponding apparatus.

In certain embodiments according to the present invention, detecting the values range takes place without the user being involved.

In some embodiments according to the present invention, detecting the values range does not take place before or only after the beginning of the treatment; in certain embodiments according to the present invention, detecting does not take place before or only after inserting or using a source of substituate solution.

In certain embodiments according to the present invention, detecting the values range takes place by taking a calcium content or a calcium concentration of a substituate solution which is used during or for the extracorporeal treatment of the blood into account, into mathematical consideration, into consideration or based on a calcium content or a calcium concentration of a substituate solution which is used during or for the extracorporeal treatment of the blood.

In some embodiments according to the present invention, suitable, optionally correspondingly configured or programmed apparatuses are provided for executing some, a few, an arbitrary number or all of the steps or substeps of the method according to the present invention.

In some embodiments according to the present invention, "controlling" is to be understood as "regulating." Both terms are equally encompassed by the present invention, wherever recognized as being executable for the person skilled in the art. Therefore, when there is mention of a control device or controlling, a regulation device or regulating may also be interpreted, if technically logical.

In certain embodiments according to the present invention, the method encompasses determining a value regarded as the lowest permissible value—hereafter sometimes also referred to as "lower threshold value" or "minimum calcium dose" and therefore to be understood as synonyms whenever this seems useful for the person skilled in the art—of the setting range, particularly to a value equal to or higher than zero.

In some embodiments according to the present invention, the method encompasses—in particular automatically—recognizing a blood treatment mode set or running in the apparatus for extracorporeally treating blood. It is thereby detected that a blood treatment mode is set or runs in which a substitution takes place by substituate, a calculation of the required calcium balance by the method according to the present invention may advantageously automatically take place. In particular, a calcium content of the utilized substituate may hereby advantageously automatically also be taken into account.

In some embodiments according to the present invention, the method encompasses detecting the value regarded as the lowest permissible lower threshold value of the range of settings. As in using a calcium-containing substitution solution or substituate solution a calcium substitution or calcium administration already takes place by the substituate, a calcium dosage is already more than 0.0 mmol/l due to the calcium amount already applied by the substitution solution. Assuming a step range of 0.1 mmol/l, the minimum calcium dose is already 0.1 mmol/l.

In some embodiments according to the present invention, the method encompasses detecting the value regarded as the lowest permissible lower threshold value of the range of settings—or the lowest threshold value of the range of settings regarded as permissible—according to Formula (1):

$$\text{Ca\_Dosis\_min} = \frac{[Ca]\_Sub * Q\_Sub + [Ca]\_Lsg * Q\_Ca\_min}{Q\_Fil + Q\_Ca\_min}$$

in which Ca_Dosis_min is the minimum calcium dose or the value regarded as the lowest permissible value or the lower threshold value of the range of values; [Ca]_Sub is the calcium concentration of the substituate; Q_Sub is the substituate flow; [Ca]_Lsg is the calcium concentration of the calcium solution; Q_Ca_min is the minimum calcium flow; and Q_Fil is the filtrate flow. For illustration purposes, in formula (1), the filtrate flow Q_Fil is defined here as the flow of the filtrate out of the filter which is reduced by the share of the filtrate that compensates for the volume infused with the calcium flow (Q_Ca). In fact, in the process, the flow that compensates for the volume infused with the calcium flow (Q_Ca) flows through the filtrate line in addition to the filtrate flow defined here.

The filtrate flow (Q_Fil) thus defined thereby corresponds in certain embodiments according to the present invention to the sum of substituate flow (Q_Sub), dialysate flow (Q_Dia), citrate flow (Q_Ci), net flow of the ultrafiltration (Q_UF), and heparin flow (Q_Hep). However, the filtrate flow may in other embodiments according to the present invention correspond to a sum of two or more of the flows mentioned above, in arbitrary combinations. In some embodiments according to the present invention, the flows that, added up, yield the filtrate flow are not limited to the flows named here. For example, in an embodiment of a treatment apparatus with, for example, a phosphate pump, also a phosphate flow or a corresponding compensating current may add to the sum which makes up the filtrate flow.

The filtrate flow is in some embodiments according to the present invention the flow of that liquid which is generated in the treatment apparatus. This flow is, if applicable, reduced by the share that compensates for the volume infused with the calcium flow.

The flows named above—and also a calcium flow—may each be flows or rates that are calculated and set or detected at the corresponding pumps.

When or if the minimum possible calcium flow (Q_Ca) corresponds to a stop or a complete halt of the calcium flow, Q_Ca=0 applies. Formula (1) may therefore also be used as Formula (1'):

$$\text{Ca\_Dosis\_min} = \frac{[Ca]\_Sub * Q\_Sub}{Q\_Fil}$$

in the corresponding embodiments according to the present invention.

As the heparin flow (Q_Hep) is often very low, Q_Hep may in certain embodiments according to the present invention be neglected or determined to be zero and then also does not contribute to or is not included in the filtrate flow (Q_Fil).

The value calculated by the formula (1) or (1') is in certain embodiments according to the present invention rounded up to full tenths mmol/l. The latter may advantageously and optionally significantly reduce the implementation effort and/or the control effort.

Formula (1) may be derived from the consideration that in defining the calcium dose for a calcium balance the whole calcium administration has to be taken into account, and that the minimum possible calcium dose is reached with a minimum possible calcium flow of zero, see formula (2):

$$\text{Ca\_Dosis} = \frac{[Ca]\_Sub * Q\_Sub + [Ca]\_Lsg * Q\_Ca}{Q\_Fil + Q\_Ca}$$

The denominator of formula (2) indicates the flow of the filtrate out of the filter and is higher by the requested water removal (Q_UF) than the sum of all flows (in particular of substituate, dialysate, citrate and heparin (each flow and particularly a heparin flow is only taken into account if the administration of the corresponding fluid or substance as, e.g., heparin takes place at all here)) that are applied in the direction towards the extracorporeal blood circuit, including the calcium flow.

Formula (1) hereby recognizably derives from formula (2) in the event that the flow of calcium Q_Ca equals the minimum possible calcium flow Q_Ca_min or is correspondingly assumed. In this case, a limiting value in the sense of a minimum or minimum possible dose is obtained by formula (1). This is obtained, if or when the calcium supply from a calcium source, which takes place for the purpose of the calcium balance, is minimized.

A minimized calcium flow or a minimized calcium supply is presently to be understood as the flow that is generated by a calcium pump, then, when the calcium pump is set to the—in its normal use—lowest possible flow setting or flow rate. In this setting, in which the pump is not completely shut off and in which the flow generated by the pump is thus not zero, the resulting calcium flow is also referred to as the "minimum possible" calcium flow Q_Ca_min in association with the present invention.

From the above-mentioned formulas, the following formula (3) is derived for the flow Q_Ca of the calcium solution which usually has the dimension [ml/h]:

$$Q\_Ca = \frac{\text{Ca\_Dosis} * Q\_Fil - [Ca]\_Sub * Q\_Sub}{[Ca]\_Lsg - \text{Ca\_Dosis}}$$

The calcium flow Q_Ca may be used according to the present invention for controlling or regulating the calcium pump, as is intended in certain embodiments according to the present invention.

A calcium dose or Ca-dose is understood as an amount of calcium in relation to a liquid volume. In some embodiments according to the invention, a calcium dose or Ca-dose is understood as the relation of calcium (in millimole [mmol]) to the filtrate, effluent or outflow (in liter [l]). Here, the terms filtrate, effluent and outflow are presently used synonymously. They each mean hereby the mixture of used dialysate and liquid which was filtrated through the membrane of the filter and which is discarded during or after the treatment.

The filtrate is in some embodiments according to the present invention understood as the sum of all liquids that are discarded during or after the treatment (e.g., the whole effluent). In some embodiments according to the present invention, the calcium flow or a compensation flow corresponding to it is explicitly not included; in others, however, it is included. In certain embodiments according to the present invention, the heparin flow or a compensation flow corresponding to it is explicitly not included; in others, however, it is included.

A calcium dose is in some embodiments according to the present invention the overall calcium amount that was infused into the extracorporeal blood circuit (i.e., the sum of the calcium from the substitution solution and the calcium from the calcium solution that was added by the dispensing device for the purpose of calcium balance) in relation to the generated amount of filtrate (or the volume conveyed by the filtrate pump).

In some embodiments according to the present invention, the method allows setting the calcium dosage, amount or concentration by the user or operator of the apparatus or the dispensing device explicitly only in the range of settings and/or not below the lower value regarded as the lowest permissible value or threshold value.

This may be ensured in that other values than the permitted values will not be displayed and thus will not be made selectable. It may further be ensured by outputting warnings, alarms or error messages if a non-permissible value is entered or is intended to be entered by the user or operator.

This way, a harmful, intentional or unintentional, setting by the user may advantageously be prevented. Also, it may be possible to prevent avoidable alarms this way.

In some embodiments according to the present invention, the method according to the present invention encompasses outputting a message after having exchanged or when exchanging a receptacle for the utilized substitute or after changing, when recognizing a change or when a change is planned of the composition, the calcium content or calcium concentration of the utilized substitute.

This way, it may advantageously be ensured that a calcium concentration that varies between different products of substitution solutions—which, if applicable, are even obtained from different producers—is reliably taken into account. The message that is output after or during exchanging a receptacle for the utilized substitute enables a manual or—after entering certain information regarding the substitution solution used from now on—automatic adjustment of the calcium dose that is added by the dispensing device.

A setting range for the calcium concentration of the utilized substitution solution that is provided in certain embodiments according to the present invention encompasses values between 1.00 mmol/l and 2.00 mmol/l. Other ranges of values are, however, also encompassed by the present invention. An incremental range that is provided in some embodiments is in increments of 0.25 mmol/l. A default setting or base setting for the substitution solution may be 1.5 mmol/l, if provided. Each default value may be changeable by the user and/or automatically.

In some embodiments according to the present invention, the method encompasses outputting a message which appears in the course of changing or exchanging the substitute bag or in conjunction herewith, and signals to the user which calcium concentration the substitute solution to be used must have. The message may be displayed on a monitor. This message may be integrated into a message that a change of the substitute bag is required. Such information may advantageously contribute to the safety of the treatment.

In certain embodiments according to the present invention, the method encompasses adjusting the value regarded as the lowest permissible value of the range of values or the lower threshold value due to a change in the flow rate of the blood pump and/or the dialysate pump or due to a change in the flows resulting from their activities.

Adjusting the value regarded as the lowest permissible value or the lower threshold value in certain embodiments according to the present invention advantageously takes place automatically, i.e., by the control or by the machine, and without the support of the user. This way, an unnecessary intervention by the user will advantageously not happen, with consequent advantages.

Adjusting the value regarded as the lowest permissible lower value or the lower threshold value in certain embodiments according to the present invention means in some cases raising the value or the threshold value.

In some embodiments according to the present invention, the method encompasses—permanently or temporarily—reducing the rate or the flow by which substitute or substitute solution is supplied to the extracorporeal blood circuit. In reducing or in detecting how much or to what extent it is reduced, a given, expected or planned—permanent or temporary—reduction of the blood flow present within the extracorporeal blood circuit is taken into account, e.g., by way of calculation. This may advantageously contribute to preventing an excessive hemoconcentration of the blood at the outlet of the filter because a high hemoconcentration may increase the risk of coagulation in the extracorporeal blood circuit.

In some embodiments according to the present invention, the method encompasses permitting lowering the calcium dose added by the dispensing device below the lower value formerly regarded as the lowest permissible value or below the value formerly regarded as lower threshold value of the setting range by the user, if—or when—, after changing the blood flow, the minimum calcium dose that results from changing is lower than before changing. This advantageously enables relaxing or dismissing a restriction that was formerly recognized as being necessary. Thus, it is afterwards up to the user—or the machine, when automatically adjusting—to use the now approved or permissible setup possibility (for the first time or, if applicable, again).

A value formerly regarded as the lowest permissible lower value or lower threshold value is in certain embodiments according to the present invention each a value which in a previous calculation or determination according to the method according to the present invention was fixed, calculated, set, detected, determined or established as such. In some embodiments according to the present invention, the value before is a preceding or the latest value or threshold value that was fixed, calculated, set or detected according to the present invention.

In some of these embodiments, it may be provided that a corresponding message is output to the user.

A message as mentioned herein may in certain embodiments according to the present invention be an optical or acoustical alarm, a text in a display window or the like, as well as combinations hereof.

In certain embodiments according to the present invention, the user interface comprises a display which is provided and/or controlled in order to display the value regarded as the lowest permissible lower value or the lower threshold value.

In certain embodiments according to the present invention, it is provided to specify a value regarded as the highest permissible upper value or an upper threshold value or the maximum calcium dose additionally or alternatively to the value regarded as the lowest permissible lower value or the lower threshold value or the minimum calcium dose. Everything that is said herein regarding the value regarded as the lowest permissible lower value or the lower threshold value or the minimum calcium dose, according to the present invention, also applies for the value regarded as the highest permissible upper value or an upper threshold value or the maximum calcium dose and is covered by the present invention, as far as this is recognizable by the person skilled in the art to be useful and/or executable.

In some embodiments according to the present invention, the apparatus is embodied as dialysis apparatus, in particular as hemodiafiltration apparatus or hemofiltration apparatus.

In certain embodiments according to the present invention, the apparatus is embodied as dialysis apparatus which is embodied and provided for blood treatment both by hemodiafiltration and by hemofiltration and optionally further treatment options.

For example, instead of a hemofiltration under Ci-Ca anticoagulation (e.g., CVVHD: continuous veno-venous hemodialysis) that is already implemented on the machine side, also a hemodiafiltration under Ci-Ca anticoagulation (e.g., CVVHDF: continuous veno-venous hemodiafiltration) may be performed with an apparatus according to the present invention. The required adjustments to the apparatus for the one or the other of these two methods may hereby be kept so low, in particular in using a user interface according to the present invention, that a selection of the one method does not require a considerable change or readaptation by the user as measured by the selection of the other method.

In certain embodiments according to the present invention, the hemodiafiltration is performed under Ci-Ca anticoagulation (e.g., CVVHDF) with a substitution (e.g., by a "multi-Bic" solution by the applicant) in postdilution. The corresponding requirements for controls, lines and so on are hereby ensured or provided.

Certain embodiments according to the present invention comprise one or more of the following advantages besides the advantages mentioned above.

In hemodiafiltration procedures, more liquid than clinically required for draining is withdrawn from the blood. This way, uremic toxins may be withdrawn from the blood at a higher level. The liquid balance is compensated for by introducing substituate into the extracorporeal blood circuit. As the utilized substitution solution contains or may contain calcium, the calcium contained in the substitution solution is advantageously taken into account according to the present invention with a calcium balance.

In certain embodiments according to the present invention, the method advantageously allows resolving the contradiction or offering a solution for the fact that when the calcium is balanced also the calcium contained in a hemofiltration or in a substituate is taken into account and additionally that in certain of such constellations and parameter characteristics the calcium flow itself or based on the mathematical formula used should by way of calculation have to be set to be negative. The solution according to the present invention in these embodiments is giving a technically useful and realizable solution—unlike the mathematically required, but technically non-useful or impossible solution. This solution may be keeping the calcium flow on a minimum value.

The present invention further offers in some embodiments a markedly user-friendly implementation of the method according to the present invention. This advantage is also supported in that the user may work with user interfaces of the utilized treatment apparatus that are already known. The user interfaces in question differ only marginally from those that are already available to the user for another known method. The user may continue to work with the appearance or model of the user interfaces that are already known.

The present invention is exemplarily explained by the appended drawings in which identical reference numerals refer to same or identical components.

DETAILED DESCRIPTION

Figure 1:
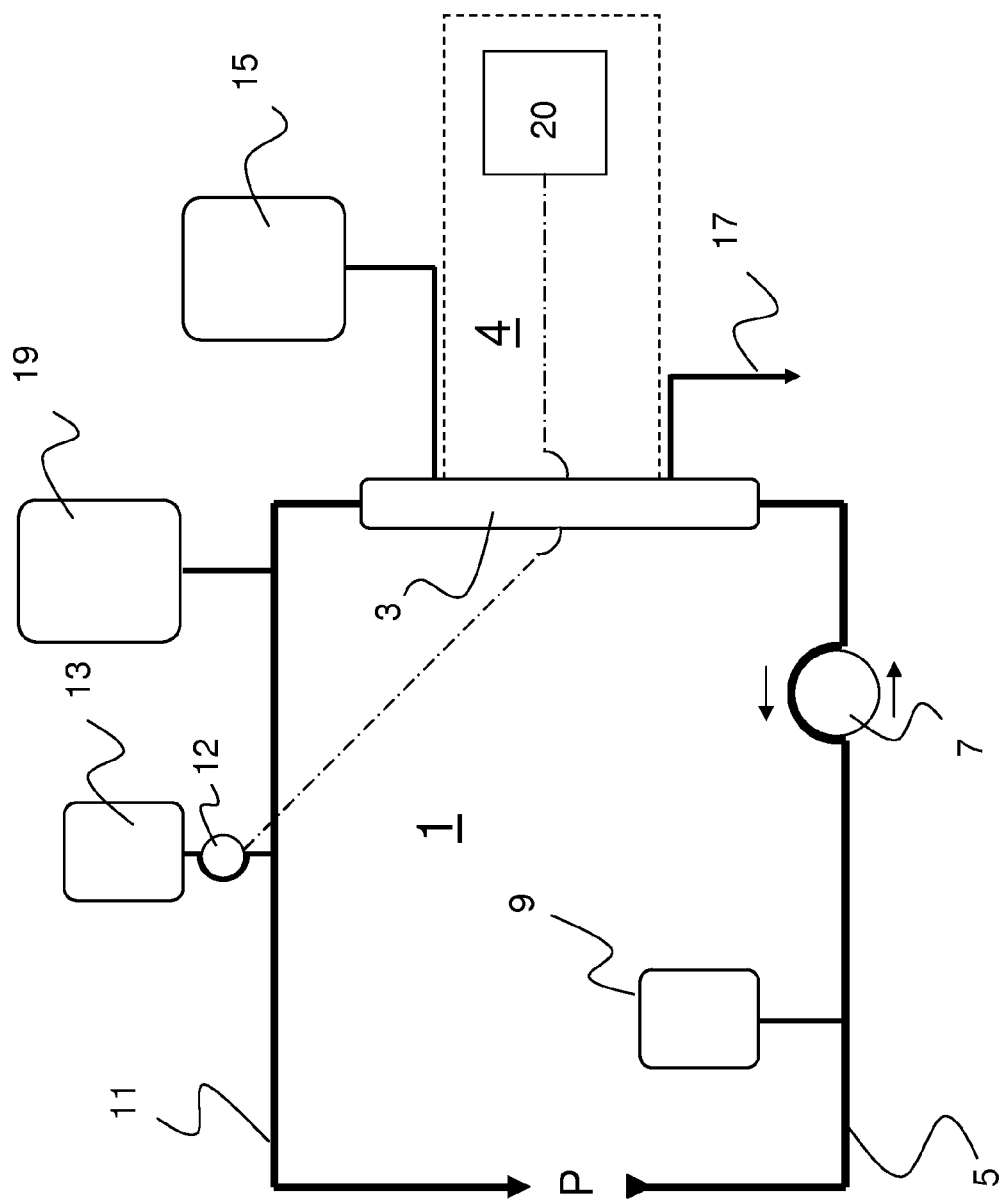
FIG. 1 shows a schematically simplified blood circuit with a dispensing device for dispensing a calcium-containing substituate according to the present invention.

FIG. 1 shows a schematically simplified blood circuit 1 with a dialysis filter or blood filter or filter 3 for executing an extracorporeal blood treatment in which blood coagulation is influenced by a citrate-calcium administration. The filter 3 is connected with an apparatus 4 (indicated by broken lines in FIG. 1) according to the present invention for extracorporeally treating blood.

The blood circuit 1 encompasses an arterial patient line or line 5 that leads away from a patient P with a blood pump 7. From a citrate solution source, here exemplarily embodied as a citrate bag 9, a citrate solution is delivered into the line 5. From the citrate solution source, four percent $Na_3$ citrate, for example, is supplied.

The blood circuit 1 further encompasses a venous patient line or line 11 that leads to the patient P. A dispensing device, here embodied as calcium pump 12, is provided for delivering a calcium solution into the line 11 from a calcium solution source, in FIG. 1 exemplarily embodied as a calcium bag 13. From the calcium solution source, a $CaCl_2$ solution, for example, is supplied. This solution may have a calcium concentration of 91 mmol/l.

The filter 3 is connected with a dialysate source, e.g., a dialysate bag 15, on the dialysate side. Dialysate, e.g., a citrate-calcium (Ci-Ca) dialysate K2, is supplied to the filter 3 from the dialysate source. The filter 3 is further connected with an outlet 17.

The line 11 is further connected with a substituate source, here in the form of a substituate bag 19. The bag 19 contains a calcium-containing substituate which may, e.g., be the product "multiBic" by the company Fresenius Medical Care Deutschland GmbH. The bag 19 is merely exemplarily—as an example for a source for substituate—arranged for dispensing the substituate in postdilution, i.e., at a location of the blood circuit 1 which in flow direction of the blood is behind the filter 3.

The blood flow set by the blood pump 7 may be set to 100 ml/min. At a pump not shown in FIG. 1 for conveying citrate solution out of the citrate bag 9, a flow of 180 ml/h may be set. At the dispensing device 12, here embodied as calcium pump, for conveying calcium solution out of the calcium bag 13 and into the extracorporeal blood circuit 1, a flow of 45 ml/h may be set. At a pump not shown in FIG. 1 for conveying dialysate out of the dialysate bag 15, a flow of 1800 ml/h may be set. At a pump not shown in FIG. 1 for conveying substituate out of the substituate bag 19, a flow of 1000 ml/h may be set. The outflow may be about 3100 ml/h. Its volume depends on the doctor's targeted net ultrafiltration rate.

It is evident from FIG. 1 that calcium is supplied to the patient P from the calcium bag 13, the dialysate bag 15 and the substituate bag 19.

Supplying the calcium or the calcium solution from the calcium bag 13 by the calcium pump 12 is controlled or regulated by a control device 20 of the apparatus 4. A corresponding signal connection is indicated as dashed-dotted line.

Figure 2:
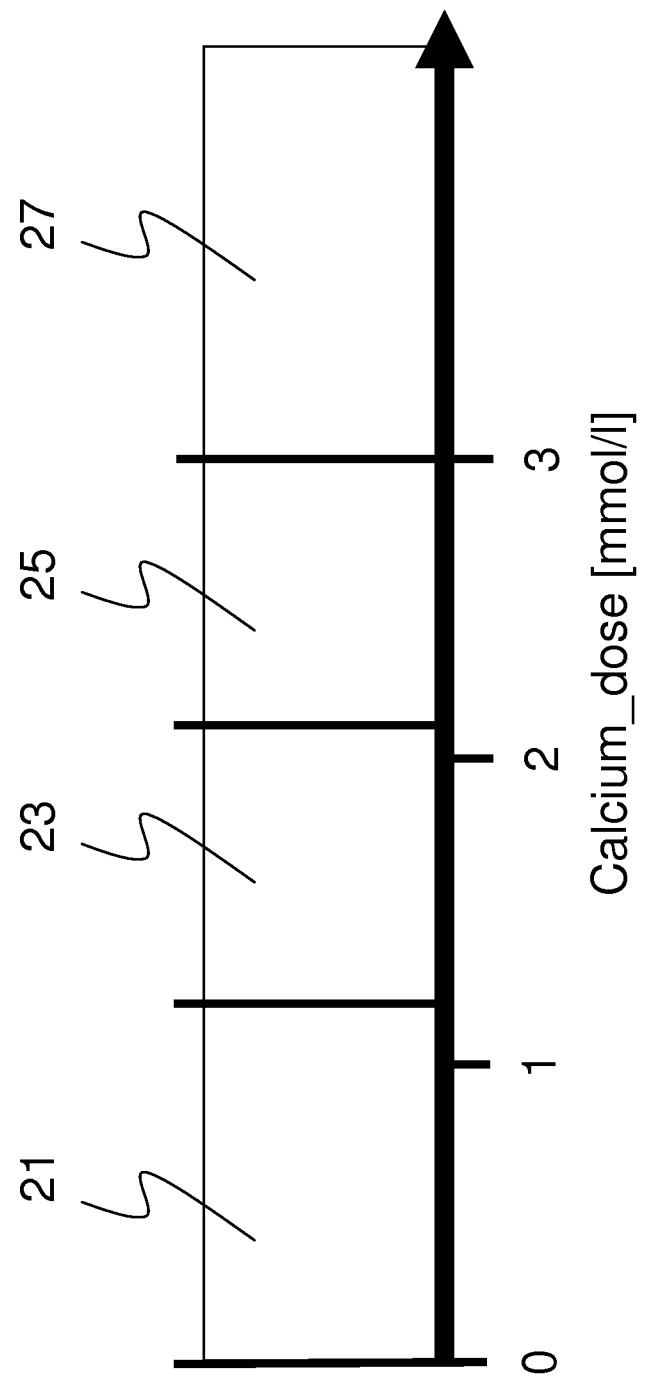
FIG. 2 shows possible setting ranges for a calcium dosage with the aim of calcium balance as well as limits of the setting range according to the present invention.

FIG. 2 exemplarily shows possible setting ranges for a calcium dosage with the purpose of calcium balance. FIG. 2 further shows limits of the setting range. The dimension of the dosage for calcium, in FIG. 2 denoted as Calcium_dose, is millimole per liter [mmol/l]. The setting range regarded as permissible or the allowed setting range for the dosage of calcium for the calcium balance in the example of FIG. 2 extends over the range of values from 0 to 3 mmol/l.

Determining a calcium dose in a range 21 corresponds to the substitution of an amount of calcium which is smaller than the expected amount of calcium that will be removed by the blood treatment. A setting in this area might lead to an undesired calcium loss, therefore setting such dosage may in certain embodiments according to the present invention take place together with displaying a message, an optical or acoustical alarm or the like. Alternatively, trying to set a calcium dose in the range 21 may also be a sign that less calcium than expected goes out of the blood through the membrane and is removed with the effluent. This may be a result of a reduced permeability of the membrane. This possibility may be pointed out to the user or the treatment apparatus in certain embodiments according to the present invention.

Setting a calcium dose which is in a range 23 would match the expectations and would not lead to a message for the user.

Setting a calcium dose which is in a range 25 corresponds to a calcium substitution above the expected calcium removal through the effluent. A message for the user about this is in certain embodiments according to the present invention provided; in others, such message is not output. It might also be pointed out that possibly a citrate accumulation is present, as it is often connected with an increased calcium substitution demand.

Setting a calcium dose which is in a range 27 would be regarded as being too high and would not be permissible. Selectability of such impermissible value for a calcium balance by the device or pump according to the present invention would not be possible according to the present invention. The user may in some embodiments according to the present invention, should he try to set calcium dose in the range 27, receive the message that he should check whether under the given circumstances a different treatment option than the set one or executed one is more suitable and optionally set this option.

Further, in some embodiments according to the present invention, an automatic adjustment of other parameters than the calcium dose may take place which may lead to a balanced calcium balance. A list with automatically permissible changes may be on file. If adjustments are necessary or even automatically performed, it is in certain embodiments provided to inform the operator about this.

Figure 3:
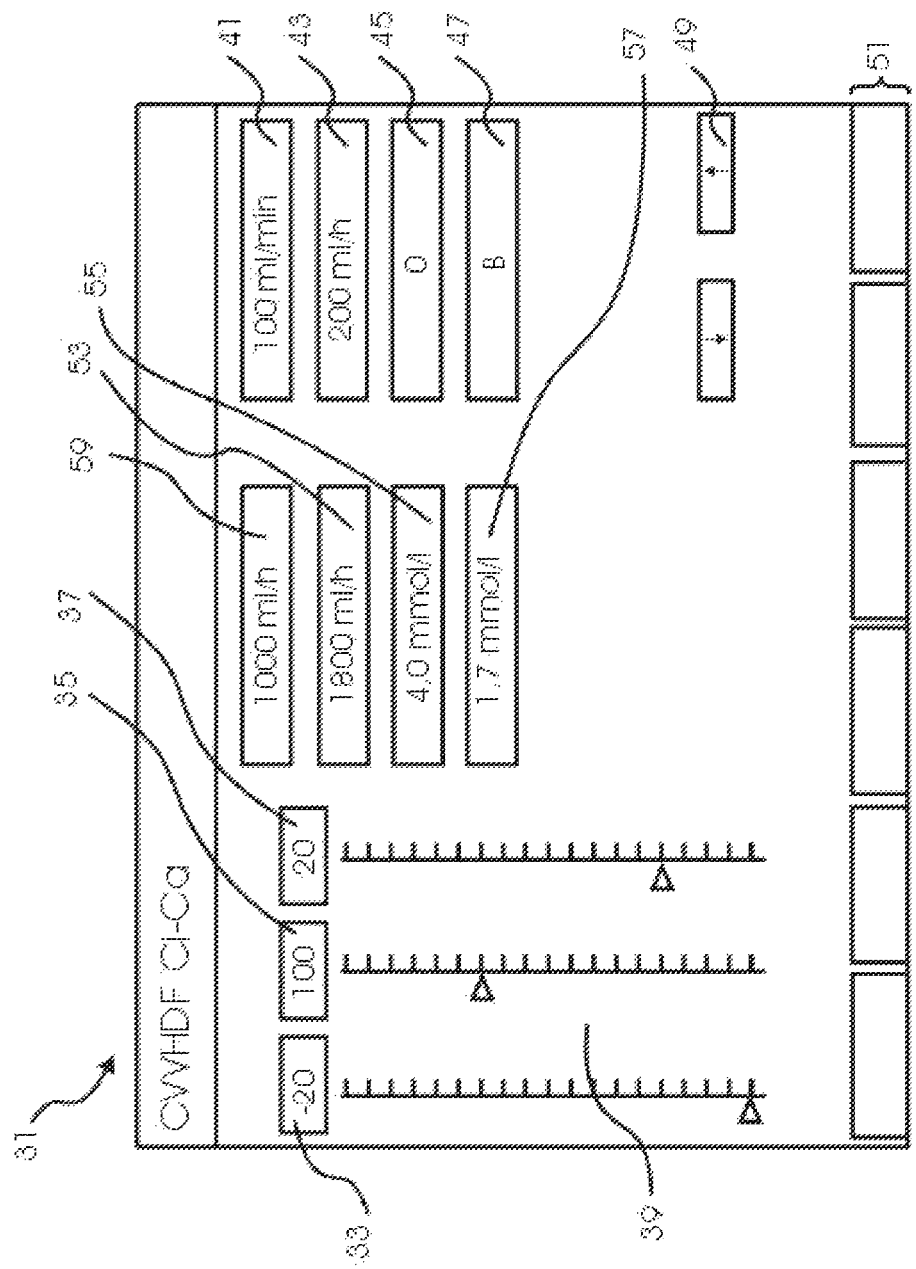
FIG. 3 shows a user interface according to the present invention for executing the method according to the present invention.

FIG. 3 shows a user interface 31 according to the present invention for executing a method according to the present invention.

From the left side of the user interface 31 indications regarding the arterial pressure 33, the venous pressure 35 and the transmembrane pressure 37, here given each in mmHg, may be taken. The corresponding values may hereby be read both expressed as numbers and as variable markings on scales 39.

The user interface 31 further comprises an indication 41 of the currently set or measured blood flow, an indication 43 of the ultrafiltration rate, an indication 45 if a continuous heparin administration takes place (here with 0 for OFF), and an indication 47 if a heparin administration takes place via bolus (here with B for "bolus" set).

The user interface 31 further comprises setting possibilities 49 for a level of the venous bubble trap and control interfaces 51 for displaying or controlling further treatment data or treatment options.

Additionally, the user interface 31 comprises a display 53 for displaying the set dialysate flow (corresponding to the dialysate rate), a display 55 for displaying the set citrate flow in relation to the blood flow, and a display 57 for displaying the set calcium flow in relation to the filtrate flow. All or some of the displays mentioned above or hereafter may in certain embodiments according to the present invention also serve for changing the set flow rates. For example, they may be adjustable by touching the corresponding display surfaces.

In the above description, the user interface 31 does not differ from an already known user interface as may be used also for a different treatment option such as the CVVHD (continuous veno-venous hemodialysis) in combination with citrate-calcium anticoagulation.

What is new or added, however, is the display 59 of the substituate flow. The user interface 31 thus additionally encompasses the indication which is relevant for executing a method known as CVVHDF (continuous veno-venous hemodiafiltration) in combination with citrate-calcium anticoagulation, as is indicated in the upper left corner of the user interface 31.

The user interface 31 illustrated in FIG. 3 is thus a development of a user interface as may be used with the CVVHD. The user interface 31 according to the present invention therefore advantageously differs only marginally from a user interface the user already knows from another blood treatment option. It may therefore in certain embodiments according to the present invention be easily adjusted based on a display for CVVHD to a display for CVVHDF, and vice versa. Offering a few specific displays and/or setting possibilities, more or less depending on which of the before-mentioned treatment options should be followed, may suffice. Coupled with this is the advantage that the user may use a user interface that is already known to him from performing a treatment option in an only marginally changed setup of the user interface also when performing a further treatment option or the method according to the present invention. Confusing the user may thus be prevented and the requirement that the user has to be familiar with a multitude of user interfaces can be eliminated.

If an impossibility of a set constellation of the various setting parameters (flows, calcium dose, and so on), e.g., in the sense of an in principle negative value of the calculated calcium flow out of the calcium pump, is produced when the requested value for the calcium addition by the calcium pump is set by the user, the calcium dose is in certain embodiments according to the present invention increased to zero, to the minimum settable value, a lower threshold value or to a predetermined default value that deviates herefrom. The minimum settable value is in some embodiments according to the present invention a value rounded up to a full 0.1 mmol/l. It may, e.g., be calculated according to the formula (1) or (1') given above or in a different suitable way.

Such technical impossibility of the required calcium dose (i.e., for instance, a negative value) that was determined by way of calculation may, e.g., also be taken into account in that the calcium dose that is required but not realizable in practice cannot be entered by the user. For example, the display computer, or every other suitable device, may already be programmed accordingly in order to make only useful and/or technically possible dosages selectable to the user. If the user nevertheless enters technically impossible values or at least values that are not allowed for the calcium dosage by the calcium pump, which may initially be possible in certain embodiments according to the present invention, however, not in others from the beginning, preferably a message may be output in order to inform the user of, e.g., the impossibility.

In certain embodiments according to the present invention, a message for the user is output whenever a setting of the calcium dose that was set on the machine side, i.e., automatically, deviates from the one the user has requested or has tried to enter. This may contribute to the user's understanding of the machine's behavior.

In some embodiments according to the present invention, the calcium dose may automatically be set to zero, a minimum value or the value resulting by way of calculation (e.g., according to formula (1) or (1')), if or when setting parameters other than the calcium dose, such as for example, the dialysate flow or the substituate flow, which influence the calculated calcium flow, change—with or without the involvement of the user. The user may be informed about this by a message, alarm, text field, and so on.

An exception from the latest mentioned procedure is in some embodiments according to the present invention provided when or if after having achieved the balance aim, i.e., an aim for the cumulated removal of water from the blood, a stop or an end of the ultrafiltration is reached and therefore the machine transitions to a changed state (in relation to parameter value, flows and the like). In this case, the calcium dose does not have to be adjusted in certain embodiments according to the present invention. Also in this situation, the user may be informed hereof by a message, alarm, text field, and so on.

In certain embodiments according to the present invention, it is provided that before an automatic change of parameter values, e.g., for the calcium pump, valid settings for arbitrary setting parameters of the device or apparatus according to the present invention (calcium dose and others) are automatically saved by the device or apparatus according to the present invention. Using the saved values, the machine's parameters may be reset—automatically or at the user's suggestion—to the previous settings when the previous settings are again technically and medically useful, possible and desired. The user may receive a message that due to certain changes previous values may now be set again. Examples for such settings and parameters include the calcium dose, the blood flow, the dialysate flow, the substituate flow and others, without being limited hereto.

In some embodiments according to the present invention, when starting the treatment, a flag set in a previous treatment, which, e.g., is always set when the calcium dose was increased automatically, may first be initialized as deleted. The flag may be set when the user enters a calcium dose. By setting the flag, the previously valid value of the calcium dose is at least temporarily saved. If or when the flag is set and if or when decreasing the calcium dose is possible or increasing the calcium dose is necessary or advisable after changing another parameter (optionally except for automatically decreasing the ultrafiltration rate to zero when the balance aim is achieved), a message to the user may be output that he may now decrease the calcium dose. The flag may subsequently be deleted. Alternatively, such adjustment may also take place automatically.

In some embodiments according to the present invention, the selection of the calcium dose is limited to a countable finite number of dose levels. In these embodiments, setting or controlling the lowest possible calcium dose, as it was calculated, e.g., by formula (1) or (1'), is not provided or not provided in each case. In these embodiments, e.g., 0.1 mmol/l or 0.2 mmol/l may be provided as setting width or setting increments which has advantageously proven effective. Therefore, in some embodiments according to the present invention, an increment of 0.1 mmol/l or 0.2 mmol/l is provided for the available setting steps. The limitation of the possible adjustment by or to at least 0.1 mmol/l or 0.2 mmol/l advantageously allows for a little time-consuming preparation of the hardware utilized in the treatment, in particular of the dispensing device by which the calcium balance takes place, and its control. Furthermore, this allows for a design of the user interface in which the smallest setting steps on the one hand enable individualization of the treatment, and on the other hand prevent displaying unnecessary information by waiving precision of the display that goes beyond this, which would be necessary with smaller setting steps. This advantageously makes the user interface clearer.

Hereafter, three examples of the method according to the present invention are illustrated.

EXAMPLE 1

In an exemplary initial configuration of the apparatus according to the present invention, the following applies:

| | |
|---|---|
| blood flow | 100 ml/min |
| substituate flow (Q_Sub) | 1000 ml/h |
| dialysate flow (Q_Dia) | 1800 ml/h |
| citrate dose | 4 mmol/l |
| calcium dose | 1.7 mmol/l |
| net ultrafiltration rate (Q_UF) | 100 ml/h |

Hereby, the internally calculated flows for the citrate solution is 176.47 ml/h and for the calcium solution is 37.95 ml/h.

Example 1 reflects a normal operating state.

In case the operator reduces the calcium dose now to, e.g., 1.2 mmol/l, the calcium flow changes to 22.18 ml/h with otherwise unaltered values. Informing the operator with the text "low calcium dose" may be advisable—the filter may have lost function.

If the calcium dose is reduced to 0.5 mmol/l, the calcium flow decreases to 0.38 ml/h with otherwise unaltered values. Informing the operator with the text "lower limit for calcium dose reached" may be advisable.

If the calcium dose is reduced to 0.4 mmol/l, the calcium flow would by way of calculation have to be decreased to −2.70 ml/h to achieve a correct calcium balance with otherwise unaltered values. However, such a setting is obviously useless and is therefore not offered or permitted.

EXAMPLE 2

In a different exemplary initial configuration of the apparatus according to the present invention, the following applies:

| | |
|---|---|
| blood flow | 100 ml/min |
| substituate flow | 1000 ml/h |
| dialysate flow | 1800 ml/h |
| citrate dose | 4 mmol/l |
| calcium dose | 0.7 mmol/l |
| net ultrafiltration rate | 100 ml/h |

Hereby, the internally calculated flows for the citrate solution is 176.47 ml/h and for the calcium solution is 6.58 ml/h.

The calcium dose is hereby low; however, it is still permissible due to the high dialysate flow. Yet, by reducing the dialysate flow, a limit of the calcium dose may be reached, as can be seen hereafter.

If the operator reduces the dialysate flow to, e.g., 800 ml/h, the calculated calcium flow changes to −0.47 ml/h with otherwise unaltered values. Automatically raising the calcium dose to a lowest of the possible values is advisable here, informing the operator if applicable.

After the calcium dose was automatically raised to, e.g., 0.8 mmol/l, the calcium flow increases to 1.62 ml/h. This is a permissible value.

EXAMPLE 3

In a further different exemplary initial configuration of the apparatus according to the present invention, the following applies:

| | |
|---|---:|
| blood flow | 100 ml/min |
| substituate flow | 600 ml/h |
| dialysate flow | 1800 ml/h |
| citrate dose | 4 mmol/l |
| calcium dose | 0.4 mmol/l |
| net ultrafiltration rate | 100 ml/h |

Hereby, the internally calculated flows for the citrate solution is 176.47 ml/h and for the calcium solution is 1.71 ml/h.

The calcium dose is hereby low; however, it is still permissible due to the low substituate flow. Yet, by raising the substituate flow, a limit of the calcium dose may be reached, as can be seen hereafter.

If the operator raises the substituate flow to, e.g., 1000 ml/h, the calcium flow calculated to be required for achieving a calcium balance changes to −2.70 ml/h with otherwise unaltered values. Automatically raising the calcium dose to a lowest of the possible values is here also advisable, informing the operator if applicable.

After the calcium dose was automatically raised to, e.g., 0.5 mmol/l, the calcium flow increases to 0.38 ml/h with otherwise unaltered values. This is a permissible value.

What is claimed is:

1. A user interface for a blood treatment apparatus having an extracorporeal blood circuit, comprising:
    a control device;
    an input device for inputting one of a calcium dosage, a calcium amount and a calcium concentration, wherein an addition of the one of the calcium dosage, the calcium amount and the calcium concentration is effected by the control device; and
    a display for displaying a value determined as a lowest permissible value;
    wherein the blood treatment apparatus includes:
        a substituate source for providing a substituate solution into the extracorporeal blood circuit; and
        a dispensing device for dispensing a calcium solution into the extracorporeal blood circuit,
    wherein the control device is configured to execute a method for controlling the apparatus while adding citrate for anticoagulation, the method comprising:
        outputting a signal to the dispensing device for altering a setting of the dispensing device, wherein the setting is at least one of corresponding to or effecting an addition of one of the calcium solution, the calcium dosage, the calcium concentration, the calcium amount, or a calcium rate;
        defining or altering the outputted signal based on one of a calcium content or a calcium concentration of the substituate solution of the substituate source used in extracorporeally treating the blood;
        automatically determining a range of permissible settings for the calcium introduced or to be introduced into the extracorporeal blood circuit by the dispensing device;
        determining the value as the lowest permissible value of the setting range, the lowest permissible value being equal to or greater than zero; and
        allowing the setting of:
            (i) one of the calcium dosage, the calcium amount or the calcium concentration by a user of the apparatus either only in the range of permissible values of the setting range or not below the value determined as the lowest permissible value, or
            (ii) one of the calcium dosage, the calcium amount or the calcium concentration automatically to the value determined as the lowest permissible value.

2. The user interface according to claim 1, wherein the method further comprises:
    recognizing one of a set blood treatment mode and a running blood treatment mode in the apparatus for extracorporeally treating blood.

3. The user interface according to claim 1, wherein the method further comprises:
    determining the lowest permissible value of the setting range according to one of (a) the formula:

$$Ca\_Dosis\_min = \frac{[Ca]\_Sub * Q\_Sub + [Ca]\_Lsg * Q\_Ca\_min}{Q\_Fil + Q\_Ca\_min}$$

and (b) the formula:

$$Ca\_Dosis\_min = \frac{[Ca]\_Sub * Q\_Sub}{Q\_Fil}$$

wherein Q_Fil is a sum of at least two flows from the group consisting of Q_Sub, Q_Dia, Q_Ci, Q_Hep, and Q_UF;
   where Ca_Dosis_min is one of a minimum calcium dose and a lower value of a values range regarded as the lowest permissible value;
   where [Ca]_Sub is a calcium concentration of the substituate solution;
   where [Ca]_Lsg is a calcium concentration of the calcium solution;
   where Q_Fil is filtrate flow;
   where Q_Sub is substituate flow;
   where Q_Dia is dialysate flow;
   where Q_Ca_min is minimum calcium flow;
   where Q_Ca is calcium flow;
   where Q_Ci is citrate flow;
   where Q_Hep is heparin flow; and
   where Q_UF is net flow of ultrafiltration.

4. The user interface according to claim 1, wherein the method further comprises:
    outputting a message one of (a) one of after and during exchanging of a receptacle for the substituate solution, and (b) when changing one of a composition, the calcium content, and the calcium concentration of the substituate solution.

5. The user interface according to claim 1, wherein the method further comprises:
    adjusting the lowest permissible value based on a change in a flow rate of at least one of a blood pump, a dialysate pump, and a different pump of the apparatus.

6. The user interface according to claim 1, wherein the method further comprises:
    reducing a rate at which the substituate solution is supplied to the extracorporeal blood circuit based on reduced blood flow in the extracorporeal blood circuit.

7. The user interface according to claim 1, wherein the method further comprises:
  permitting decreasing the calcium dosage added by the dispensing device below the lowest permissible value of the setting range by a user, if, after changing a blood flow, a minimum calcium dose that results from the changing is lower than before the changing.

8. An apparatus for extracorporeally treating blood, the apparatus comprising the user interface according to claim 1.

9. The apparatus according to claim 8, wherein the apparatus is one of a dialysis apparatus, a hemodiafiltration apparatus and a hemofiltration apparatus.

10. The apparatus according to claim 8, wherein the apparatus is a dialysis apparatus configured for blood treatment by hemodiafiltration and by hemofiltration.

\* \* \* \* \*